United States Patent [19]
Douglass et al.

[11] Patent Number: 6,151,405
[45] Date of Patent: Nov. 21, 2000

[54] SYSTEM AND METHOD FOR CELLULAR SPECIMEN GRADING

[75] Inventors: James Douglass, Indialantic; Thomas J. Riding, West Melbourne, both of Fla.; William J. Decker, San Juan Capistrano, Calif.

[73] Assignee: ChromaVision Medical Systems, Inc., San Juan Capistrano, Calif.

[21] Appl. No.: 08/827,268

[22] Filed: Mar. 28, 1997

Related U.S. Application Data

[63] Continuation-in-part of application No. 08/758,436, Nov. 29, 1996.

[51] Int. Cl.⁷ .................................................. G06K 9/00
[52] U.S. Cl. .......................... 382/133; 382/128; 382/130; 382/134; 382/162; 356/39
[58] Field of Search ................................ 382/133, 130, 382/128, 134, 162, 165; 128/922; 356/39

[56] References Cited

U.S. PATENT DOCUMENTS

| | | | |
|---|---|---|---|
| 3,824,393 | 7/1974 | Brain | 250/222.1 |
| 5,202,931 | 4/1993 | Bacus | 382/133 |
| 5,257,182 | 10/1993 | Luck et al. | 382/224 |
| 5,268,966 | 12/1993 | Kasdan | 382/133 |
| 5,287,272 | 2/1994 | Rutenberg et al. | 382/224 |
| 5,333,207 | 7/1994 | Rutenberg | 382/6 |
| 5,585,469 | 12/1996 | Kojima et al. | 534/573 |
| 5,625,705 | 4/1997 | Recht | 382/128 |
| 5,740,270 | 4/1998 | Rutenberg et al. | 382/133 |

Primary Examiner—Leo H. Boudreau
Assistant Examiner—Kanji Patel
Attorney, Agent, or Firm—Fish & Richardson P.C.

[57] ABSTRACT

The system and method for evaluating the amount of marker identifying precipitate in a cellular specimen on a microscope slide is disclosed. The automated microscope system performs a low magnification and high magnification scan of a cellular specimen to identify and confirm candidate objects of interest which correspond to cells containing a marker identifying precipitate. A regularly shaped area centered about a centroid computed for a candidate object of interest is used to define the pixels to be processed. A color ratio is computed for each pixel and those color ratios indicative of being dominated by the color corresponding to the marker identified precipitate are summed and normalized. The normalized color ratio is compared to at least one predetermined threshold to assign a grade to the candidate objects of interest. The grades for a predetermined number of candidate objects of interest are summed to form an aggregate score and the aggregate score is compared to a threshold. If the aggregate score exceeds a threshold, the candidate object of interest is determined to indicate the medical condition typically associated with the marker.

30 Claims, 5 Drawing Sheets

SYSTEM AND METHOD FOR CELLULAR SPECIMEN GRADING

This is a continuation-in-part of application Ser. No. 08/758,436 filed on Nov. 29, 1996.

FIELD OF THE INVENTION

This invention relates to automated analysis of cellular specimens on microscope slides, and more particularly, to automated analysis of cellular specimens containing stained markers.

BACKGROUND OF THE INVENTION

In the field of medical diagnostics including oncology, the detection, identification, quantitation and characterization of cells of interest, such as cancer cells, through testing of biological specimens is an important aspect of diagnosis. Typically, a biological specimen such as bone marrow, lymph nodes, peripheral blood, cerebrospinal fluid, urine, effusions, fine needle aspirates, peripheral blood scrapings or other materials are prepared by staining the specimen to identify cells of interest. One method of cell specimen preparation is to react a specimen with a specific probe which can be a monoclonal antibody, a polyclonal antiserum, or a nucleic acid which is reactive with a component of the cells of interest, such as tumor cells. The reaction may be detected using an enzymatic reaction, such as alkaline phosphatase or glucose oxidase or peroxidase to convert a soluble colorless substrate to a colored insoluble precipitate, or by directly conjugating a dye to the probe.

For example, substances sometimes known as markers may exist in a person's blood as a result of some medically abnormal condition. These markers may exist for such conditions as preleukemic cancers, a trisomy 21 fetus, or other known conditions which cause markers to exist in one's blood. These markers are normally not visually detectable. However, a blood cell sample may be fixed and bound with a substrate of an enzyme to produce a colored insoluble precipitate to identify the marker. The slides containing the prepared cellular specimens are then examined to evaluate the amount of the precipitate contained in the cellular specimen to determine whether the cellular specimen indicates that the condition exists in the person from which the sample was obtained.

For example, blood cells are classified into two types—red and white cells. The red cells carry oxygen in the form of hemoglobin to tissue in a person. The white cells are generally related to a person's immunity system. White blood cells are comprised of five types of which one, neutrophils, has a lobed nucleus which is typically used to identify this type of white blood cells. In response to the presence of a fetus, the neutrophil cells in the blood of a pregnant woman have an elevated level of alkaline phosphatase. If the fetus is a trisomy 21 fetus, the level of alkaline phosphatase in the neutrophils is even higher. Thus, the amount of alkaline phosphatase in the neutrophils of a pregnant woman's blood may be used as a marker for a trisomy 21 fetus. By preparing a blood specimen from a pregnant woman with a stain for identifying the alkaline phosphatase in neutrophils and a counterstain to facilitate detection of the lobed shaped nuclei of neutrophils, a pathologist may visually determine the likelihood that the fetus is a trisomy 21 fetus.

Examination of biological specimens in the past has been performed manually by either a lab technologist or a pathologist. In the manual method, a slide prepared with a biological specimen is viewed at a low magnification under a microscope to visually locate candidate cells of interest. Those areas of the slide where cells of interest are located are then viewed at a higher magnification to confirm those objects as cells of interest. The manual method is time consuming and may be susceptible to error including missing areas of the slide. In the example given above, the low magnification scan is performed to identify the neutrophils by the lobed shaped nuclei having the counterstain color.

Automated cell analysis systems have been developed to improve the speed and accuracy of the slide evaluation process. One known interactive system includes a single high power microscope objective for scanning a rack of slides, portions of which have been previously identified for assay by an operator. In that system, the operator first scans each slide at a low magnification similar to the manual method and notes the points of interest on the slide for later analysis. The operator then stores the address of the noted location and the associated function in a data file. Once the points of interest have been located and stored by the operator, the slide is then positioned in an automated analysis apparatus which acquires images of the slide at the marked points and performs an image analysis.

There are also known automated specimen analysis systems which automatically view slides located in carriers which are loaded in a hopper. The carriers are moved, one at a time, from the hopper to a motorized XY stage of the microscope. The motorized stage is operated to place one slide in the carrier under the objective turret of the microscope and the slide is scanned at a low magnification power. The view of the slide through the oculars of the microscope is captured by a camera which may either be a digital camera or an analog camera with an analog/digital (A/D) converter. The digitized image is provided to a computer subsystem coupled to the automated microscope to detect candidate objects of interest on the slide. The information regarding the candidate objects of interest is then stored and the viewing power for the objective turret is increased to a high magnification level. The slide is scanned at high magnification and an image of the slide at the high magnification level is captured by the camera, digitized, and further processed by the computer subsystem to eliminate debris and other objects which may be part of the cellular specimen which do not require analysis. The portions of the high magnification image which correspond to candidate objects of interest not eliminated by the processing at the high magnification level are then stored in a montage for viewing by a pathologist. Information identifying the slide from which the image was obtained and the location of the candidate object of interest on the slide is also recorded with the montage. If the pathologist wants to view the candidate object of interest on the slide, the pathologist may place the slide in a carrier and load it in the automated analysis system. The system then moves the slide to a position underneath the objective turret where, under high magnification, the pathologist may view the candidate object of interest to confirm the selection of the candidate object of interest for the montage.

One problem with previously known automated systems is the difficulty in evaluating the amount of a marker present in a cellular specimen. For example, neutrophil alkaline phosphatase (NAP) is typically stained to cause the insoluble product which identifies the marker to become red in color. The cellular specimen is usually counterstained to make the nuclei of the cells become blue in color. A pathologist viewing such a slide detects neutrophils by locating those cells which have a nucleus of the color, shape, and size expected for a neutrophil. The pathologist then subjectively evaluates the intensity of the red color for each located neutrophil and assigns a score to each one. The pathologist then subjectively determines whether the number of intensely red neutrophils and moderately red neutrophils are sufficient to conclude that the cellular specimen is indicative of a particular condition. For NAP, the pathologist usually grades the neutrophils with a rating of 0, 1, 2, 3, or 4 in accordance with a grading scale such as the one provided with the procedure for using the reagent kit sold by Sigma Diagnostics for demonstrating alkaline phosphatase activity in leukocytes. According to that procedure, a pathologist sums the subjectively assigned ratings for marker identifying precipitate in the first 100 neutrophils to arrive at a score which may be used to determine the relative red intensity of the neutrophils in the cellular sample. This score may then be used to determine whether the condition associated with the presence of the marker is indicated.

Previously known automated specimen analysis systems have not been able to provide grading as reliable as that possible with a trained pathologist. For example, U.S. Pat. No. 5,352,613 to Tafas et al. discloses a cytological screening method which purports to evaluate the presence and amount of such markers as NAP. However, the system of this patent has a number of limitations. For one, the perimeter of neutrophils or other candidate objects of interest must be precisely located in the images as the method of this patent computes an average optical density for each pixel within a candidate object of interest. However, where a candidate object of interest, such as a neutrophil, is overlapped by a red blood cell, the method of this patent may inaccurately define the perimeter of the candidate object of interest if it is using the red color component to define the perimeter for the candidate object of interest. When the perimeter of the candidate object of interest is not accurately defined, pixels actually in a candidate object of interest may be missed and those not actually in a candidate object of interest may be included in the computation of the density value. In fact, this patent does not indicate that the pixels for the nuclei of the cells being evaluated are excluded from the optical density measurements. In some cases, the inclusion of the nuclei pixels or exclusion of pixels actually in a cell may skew the measurements. Additionally, the method of this patent operates on a single color component of the image of the cellular specimen and, as a result, where cells may overlap, the pixel value of the single color component being analyzed may be attenuated in the light passed by the overlapped cells.

What is needed is a system which grades neutrophils containing NAP as reliably as a trained pathologist. What is needed is an automated specimen analysis system which does not rely on precise perimeter definition of candidate objects of interest in order to measure the amount of a marker identifying precipitate within a candidate object of interest. What is needed is a system which can accurately evaluate the amount of a marker identifying precipitate within a cellular specimen even though overlapping cells are present in the defined object of interest.

SUMMARY OF THE INVENTION

The limitations of previously known automated analysis systems and methods may be overcome by a system implementing the method of the present invention. The inventive method includes the steps of obtaining a color digital image of a magnified view of a cellular specimen bound to a microscope slide, processing the color digital image to identify a plurality of candidate objects of interest in the cellular specimen, identifying a centroid for each candidate object of interest, computing a color ratio of at least two color components for each pixel of an area centered about each identified centroid, computing an average color ratio for all pixels in the area centered about each centroid having a computed color ratio that exceeds a predetermined color ratio threshold, and comparing the computed average color ratio to at least one intensity threshold to evaluate the amount of marker identifying precipitate in each area centered about each centroid.

This method may be implemented by an automated analysis system which obtains digital images and processes the digital images to locate candidate objects of interest in a cellular specimen on a microscope slide. In a preferred embodiment, the system computes a ratio of two color components for the pixels in a regularly shaped area about the identified centroid. In a most preferred implementation, the area is a 70 pixel by 70 pixel area centered about the centroid. By defining a regularly shaped area about the centroid, the grading system no longer needs to traverse an irregular perimeter associated with a candidate object of interest to identify the pixels required for analysis of the object. Instead, the computation of a color ratio using at least two color components effectively includes in the evaluation only those pixels which contain evidence of the marker identifying precipitate and its relative intensity. Because the area centered about the centroid is regularly shaped, the processing of the pixels is much faster than previously known methods. Additionally, use of the ratio of two color components provides more information so the method is more accurate than those using only one color component to evaluate the amount of a marker identifying precipitate.

In the preferred implementation of the present invention, a 70 pixel by 70 pixel area around a centroid is first defined. A ratio of the red pixel intensity to the green pixel intensity for each pixel in the area is used for the evaluation of NAP in the area. The preferred ratio is a ratio of the difference between the red and green pixel components to the sum of the red and green pixel components. Because the preferred implementation does not use the absolute value of the difference, the ratio is a signed magnitude within the range of −1 to +1. When a cellular sample has been chemically assayed with a solution of napthol AS-biphosphate salt and fast red violet LB, the presence of alkaline phosphatase is indicated by the red color of the precipitate formed by hydrolysis. As a result, the preferred color ratios that indicate the presence of NAP are in the range of slightly greater than zero to +1. Consequently, all of the pixels which indicate the presence of NAP within the regularly shaped area may be identified by ratios having a positive, non-zero value.

The color ratios for those pixels having a color ratio which is both non-zero and positive are summed and then divided by the number of pixels having non-zero, positive values. This computed value is a normalized ratio in the range of zero to +1. The range from zero to +1 may be divided into five sub-regions which correspond to the 0, 1, 2, 3, and 4 score values commonly used to grade the amount of NAP in a cellular specimen. The score for 100 of these areas is computed and then summed to obtain an aggregate score for the cellular specimen. This aggregate score is then compared to a threshold to evaluate whether the amount of NAP in the cellular specimen indicates whether the person from which the specimen was obtained has the condition normally indicated by the marker.

The method and system of the present invention provide a number of benefits and advantages. For one, because regularly shaped areas are used to evaluate the area about the centroid of a candidate object of interest, the processing of the pixels in the area is much faster than if an irregularly shaped perimeter must be located and then followed to process the image data for a candidate object. The use of two color components for the color ratio permits the system and method to use a regularly shaped area as the ratio effectively identifies only those pixels in the cytoplasm of the neutrophil that contain alkaline phosphatase without having to locate and traverse an object perimeter. Additionally, the use of two color components allows a system to detect the presence of a marker even though debris or an overlapped cell may attenuate the red pixel values in the overlapped area. The reader should appreciate that the system and method of the present invention may be used to evaluate the amount of marker in any cellular specimen stained to identify the marker present in the cellular specimen. These methods include, but are not limited to, monoclonal antibodies, polyclonal antibodies, in situ hybridization, or reverse transcriptase polymeraze chain reaction (RTPCR) methods.

Another feature of the present invention is the use of a noise reducing filter used for the color ratio computation. This filter is a threshold to which the two color component difference is compared. If the two color component difference is less than the threshold, the ratio for the pixel is not computed. Preferably, this threshold is a small positive number. This noise threshold reduces the likelihood that a pixel having its two color component difference increased to a small positive number by electronic noise is evaluated for marker identifying precipitate. This filter also helps exclude pixels from a red blood cell which extends beyond an overlap area with a candidate object of interest. Thus, the filter reduces the need to accurately define the perimeter of the candidate object of interest and compensates for electronic noise in the generation of the image data.

These and other advantages and benefits of the present inventive system and method may be ascertained from the detailed description of the invention.

BRIEF DESCRIPTION OF THE DRAWINGS

The accompanying drawings, which are incorporated and constitute a part of the specification, illustrate preferred and alternative embodiments of the present invention and, together with a general description given above and the detailed description of the embodiments given below, serve to explain the principles of the present invention.

DETAILED DESCRIPTION OF THE INVENTION

Figure 1:
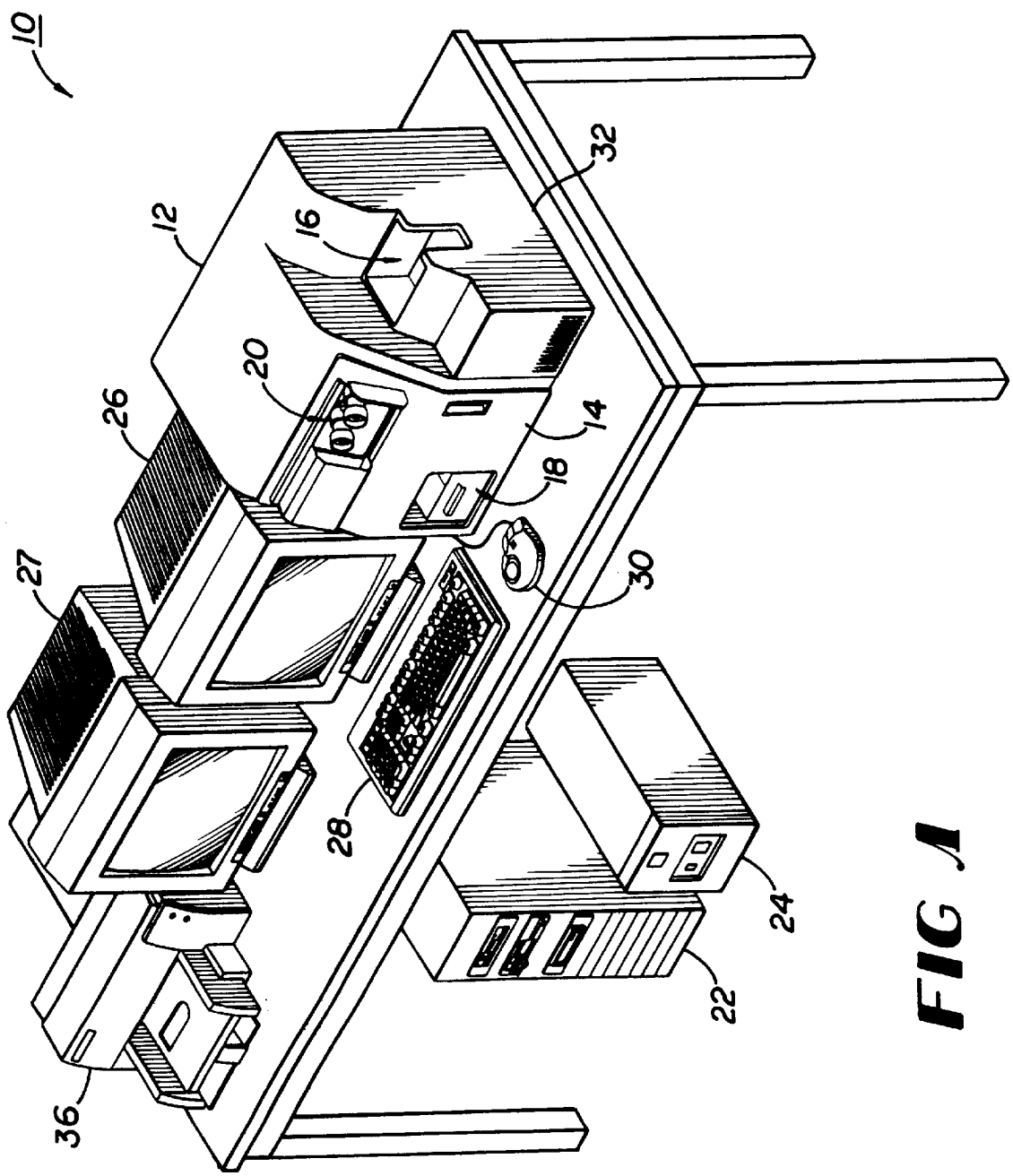
FIG. 1 is a perspective view of an apparatus for automated cell analysis embodying the present invention.
Figure 2:
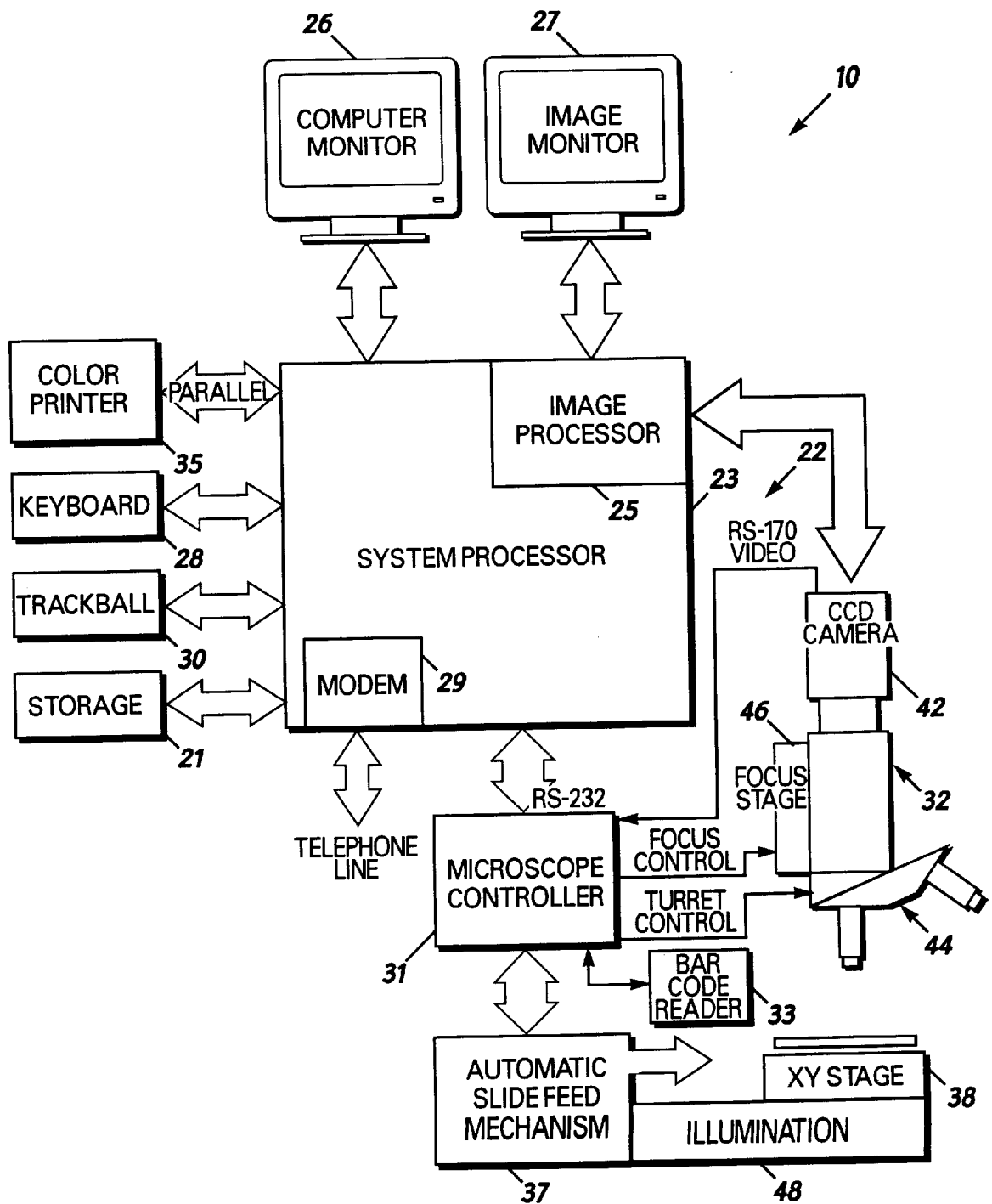
FIG. 2 is a block diagram of the apparatus shown in FIG. 1.

Referring now to the figures, an apparatus for automated cell analysis of biological specimens is generally indicated by reference numeral 10 as shown in perspective view in FIG. 1 and in block diagram form in FIG. 2. The apparatus 10 comprises a microscope subsystem 32 housed in a housing 12. The housing 12 includes a slide carrier input hopper 16 and a slide carrier output hopper 18. A door 14 in the housing 12 secures the microscope subsystem from the external environment. A computer subsystem comprises a computer 22 having a system processor 23, an image processor 25 and a communications modem 29. The computer subsystem further includes a computer monitor 26 and an image monitor 27 and other external peripherals including storage device 21, track ball device 30, keyboard 28 and color printer 35. An external power supply 24 is also shown for powering the system. Viewing oculars 20 of the microscope subsystem project from the housing 12 for operator viewing. The apparatus 10 further includes a CCD camera 42 for acquiring images through the microscope subsystem 32. Preferably, a switch is included in the system which either provides the magnified view from the objective turret 44 to oculars 20 or camera 42. A microscope controller 31 under the control of system processor 23 controls a number of microscope-subsystem functions described further in detail. An automatic slide feed mechanism 37 in conjunction with X-Y stage 38 provide automatic slide handling in the apparatus 10. An illumination light source 48 projects light onto the X-Y stage 38 which is subsequently imaged through the microscope subsystem 32 and acquired through CCD camera 42 for processing in the image processor 25. A Z stage or focus stage 46 under control of the microscope controller 31 provides displacement of the microscope subsystem in the Z plane for focusing. The microscope subsystem 32 further includes a motorized objective turret 44 for selection of objectives.

The purpose of the apparatus 10 is for the unattended automatic scanning of prepared microscope slides for the detection of candidate objects of interest, such as particular cells which may contain marker identifying precipitate, and evaluation of the amount of a marker identifying precipitate in the detected candidate objects of interest. Apparatus 10 automatically locates candidate objects of interest present in a biological specimen on the basis of color, size and shape characteristics. Grades indicative of the amount of marker identifying precipitate for the candidate objects of interest are determined and summed to generate a score for the biological specimen. This score may be used to evaluate whether the biological specimen is indicative of a medical condition typically associated with the marker that produced the marker identifying precipitate. A number of stains and counterstains are used to produce colored marker identifying precipitate in various cells and cell structures of the biological specimen. The apparatus of the present invention is used to detect this precipitate to identify candidate objects of interest.

During operation of the apparatus 10, a pathologist or laboratory technologist mounts prepared slides onto slide carriers. A slide carrier holds up to 4 slides and up to 25 slide carriers may be loaded into input hopper 16. The operator can specify the size, shape and location of the area to be scanned or alternatively, the system can automatically locate scan areas. The operator then commands the system to begin automated scanning of the slides through a graphical user interface. Unattended scanning begins with the automatic loading of the first carrier onto precision motorized X-Y stage 38. A bar code label affixed to the slide is read by a bar code reader 33 during this loading operation. Each slide is then scanned at a user selected low microscope magnification, for example, 20x, to identify candidate objects based on their color, size and shape characteristics. The X-Y locations of candidate objects are stored until scanning is completed.

After the low magnification scanning is completed, the apparatus automatically returns to each candidate object, focuses at a higher magnification, such as 60x for NAP evaluation, and captures a digitized image for further analysis to confirm the object candidate. The centroid for each confirmed cell candidate is computed and stored for evaluation of the marker identifying precipitate. Apparatus 10 then returns to the centroid for the first confirmed candidate object of interest and captures a color image of an area centered about the centroid. The pixel data for this area is processed to determine the amount of marker identifying precipitate in the area and a grade is assigned to the object. Apparatus 10 continues processing and grading areas centered about other confirmed candidate objects of interest until a predetermined number of objects have been processed. An aggregate score is then computed from the grades for the predetermined number of objects. The object grades, aggregate score and images may then be stored to a storage device 21 such as a removable hard drive or DAT tape or transmitted to a remote site for review or storage. The stored images for each slide can be viewed in a mosaic of images for further review. In addition, the pathologist or technologist can also directly view a detected cell through the microscope using oculars 20 or image monitor 27.

Figure 3:
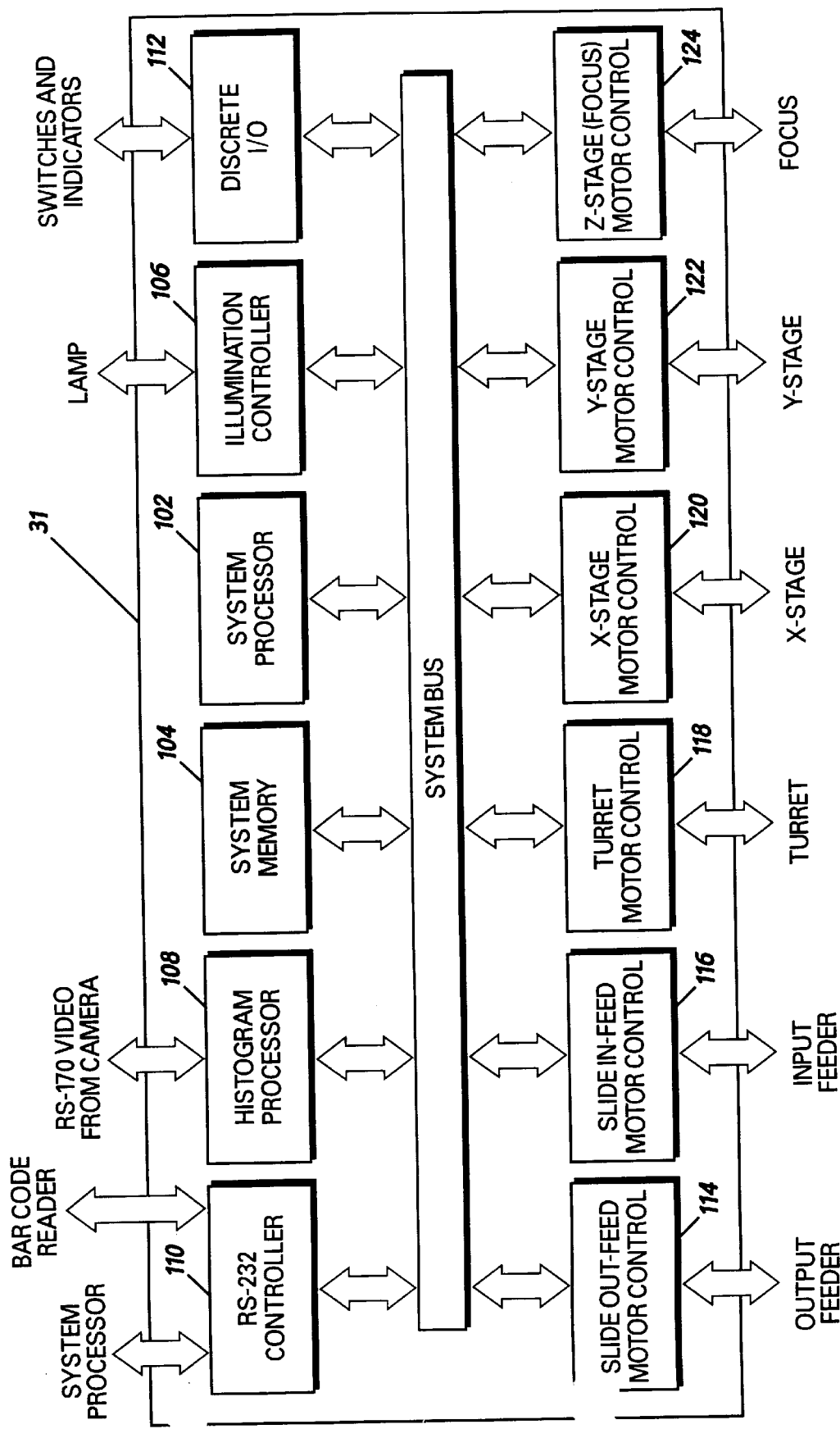
FIG. 3 is a block diagram of the microscope controller of FIG. 2.

Referring to FIG. 3, microscope controller 31 is shown in more detail. Microscope controller 31 includes a number of subsystems connected through a system bus. System processor 102 controls these subsystems and is controlled by apparatus system processor 23 through an RS 232 controller 110. System processor 102 controls a set of motor control subsystems 114 through 124 which control the input and output feeder, motorized turret 44, X-Y stage 38, and Z stage 46 (FIG. 2). Histogram processor 108 receives input from CCD camera 42 for computing variance data during the focusing operation described further herein.

System processor 102 further controls illumination controller 106 for control of substage illumination 48. The light output from the halogen light bulb which supplies illumination for the system can vary over time due to bulb aging, changes in optical alignment, and other factors. In addition, slides which have been "over stained" can reduce the camera exposure to an unacceptable level. In order to compensate for these effects, illumination controller 106 is included. This controller is used in conjunction with light control software to compensate for the variations in light level. The light control software samples the output from the camera at intervals (such as between loading of slide carriers), and commands the controller to adjust the light level to the desired levels. In this way, light control is automatic and transparent to the user and adds no additional time to system operation.

System processor 23 is preferably an IBM compatible PC with an Intel Pentium 90 MHz processor, 32 MB of RAM, and two 1 GB hard drives with one hard drive being removable. The operating system for system processor 23 is Windows for Workgroups 3.1 available from Microsoft Corporation of Redmond, Wash. Image processor 25 is preferably a Matrox Imaging Series 640 board set available from Matrox Electronics Systems, Ltd. of Dorval, Quebec, Canada. The preferred image processor is provided with support software and the Matrox Imaging Library (MIL). Microscope controller system processor 102 is an Advanced Micro Devices AMD29K device.

The low magnification image processing identifies cells having a nucleus which is stained a particular color which corresponds to the stain or counterstain used to prepare the cellular specimen. For example, a blood smear used to evaluate the presence of alkaline phosphatase in neutrophils is typically stained with a solution of napthol AS-biphosphate salt and fast red violet LB. The presence of alkaline phosphatase in a neutrophil (NAP) in the cellular specimen is indicated by the red color of the precipitate formed by hydrolysis. The specimen is usually counterstained with a counterstain such as hematoxylin to produce a blue insoluble precipitate in white blood cell nuclei. The resulting specimen from this stain/counterstain procedure results in white blood cells which may be identified by the cells having blue nuclei. These cells may be processed to identify neutrophil cells based on the shape and size of the nuclei. Thus, the low magnification processing identifies candidate objects of interest, such as neutrophils, from the color, shape, and size of objects in the image of the cellular specimen.

The processing performed by the system during the high magnification image processing further evaluates color, shape and size of the cell nucleus for each of the candidate objects of interest to eliminate objects not likely to contain the marker identifying precipitate. In a preferred implementation of the present invention for NAP, the minimum area for identifying candidate objects of interest is 14 $\mu m^2$. The preferred compactness value is for objects having a nucleus which is greater than the value 1.25. Compactness is a term indicating the shape of the perimeter of the nucleus which is well known in the field. The centroid of the identified candidate object of interest is then computed and the centroid is stored for the score processing. After a predetermined number of candidate objects of interest are confirmed and their corresponding centroids stored, score processing is performed.

In the preferred implementation, the image processing performed at the low magnification and high magnification levels is that which is disclosed in our co-pending patent application entitled METHOD AND APPARATUS FOR AUTOMATED IMAGE ANALYSIS OF BIOLOGICAL SPECIMENS, Ser. No. 08/758436 and filed on Nov. 27, 1996. The disclosure of that application is hereby expressly incorporated by reference. The color conversion, low pass filtering, thresholding, and morphological processing disclosed in that document is preferably used to identify candidate objects of interest. The centroid and morphological characteristics for a candidate object of interest, such as its size and compactness, is obtained from functions in the MIL for the preferred image processor. Although this is the preferred method for identifying and confirming candidate objects of interest in the image of a cellular specimen, other known methods may be used as long as the method identifies the location and general shape of those cells which contain the marker identifying precipitate.

Figure 4:
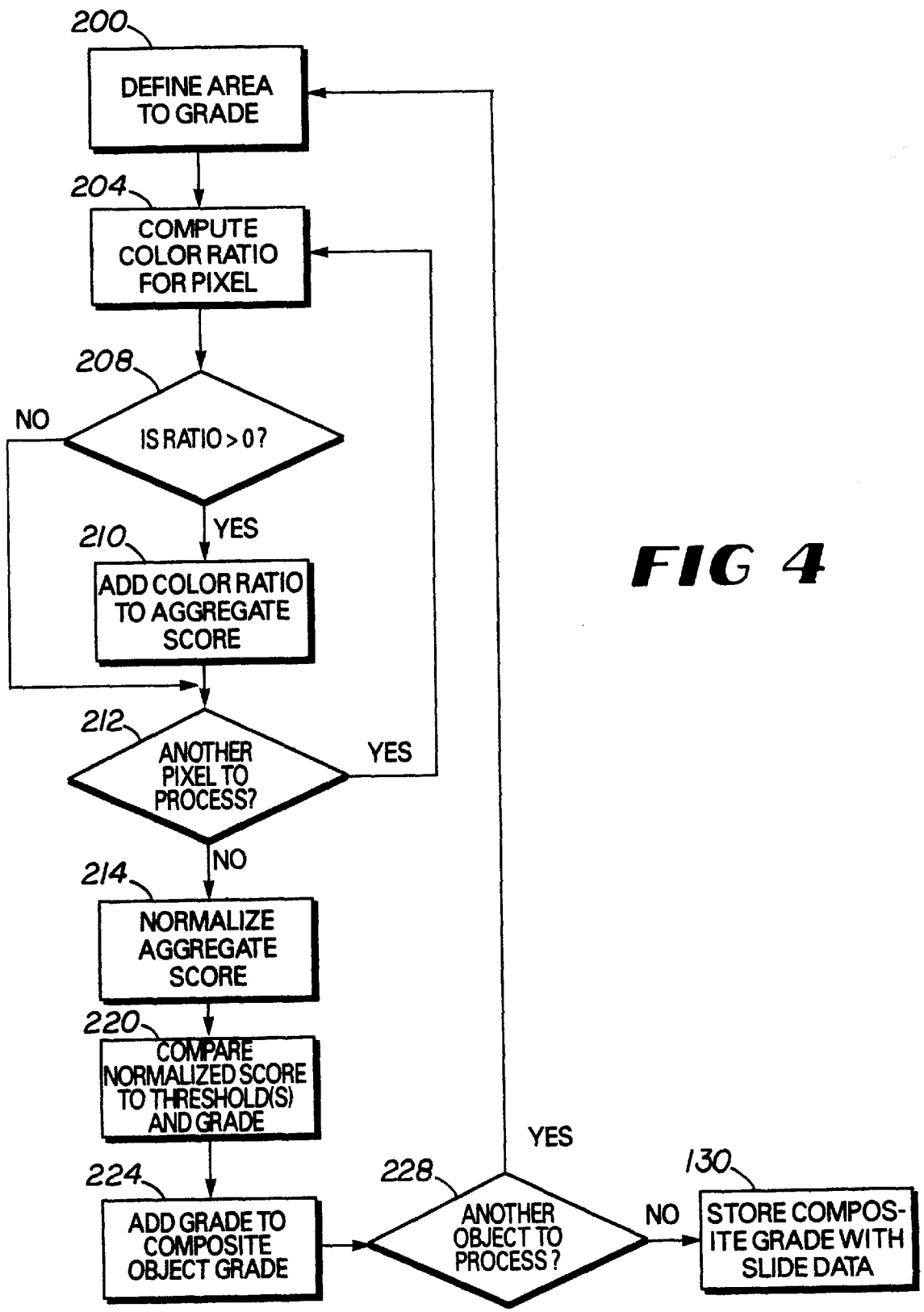
FIG. 4 is a flowchart of the preferred method for grading objects in an image of a cellular specimen obtained by the apparatus of FIG. 1.
Figure 5:
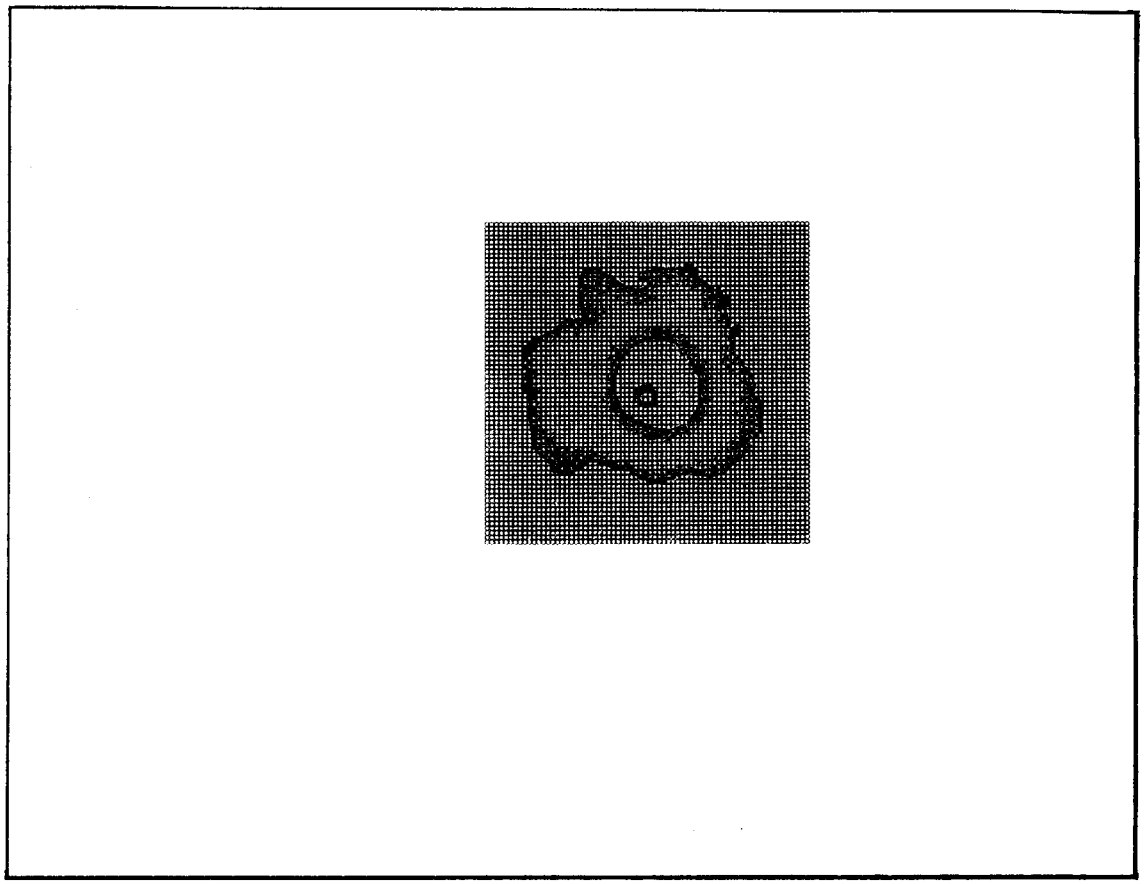
FIG. 5 is a perspective view of a regularly shaped area in an image of a cellular specimen processed by the exemplary method depicted in FIG. 3.

The method of the score processing is shown in FIG. 4. That process begins by retrieving the centroid for the first confirmed object of interest and captures the color pixel values for a regularly shaped area centered about the centroid (Block 200). The area may be any regularly shaped area that is easily traversed by known programming loop control such as two dimensional parallelograms. The most preferred regular shape is a square and the most preferred size of the square is 70 pixels×70 pixels. The regularly shaped area should be sufficiently large enough to include all of the pixels containing image data for the marker identifying precipitate that are associated with a candidate object of interest. For example, the most preferred 70 pixels×70 pixels shape corresponds to an area large enough to cover the cytoplasm and nucleus of the cell corresponding to a confirmed candidate object of interest. The most preferred area is shown in FIG. 5. As can be seen from the figure, the regular shaped area extends beyond the perimeter of the candidate object of interest so that the area centered about the centroid of the object of interest includes all of the pixels of the candidate object of interest. The reader should appreciate that any area which may be used to simplify evaluation of the amount of marker identifying precipitate in a candidate object of interest without having to define the perimeter of the candidate object of interest in order to identify the candidate object of interest pixels to be included in the evaluation is within the principles of the present invention.

A color ratio for each pixel is then computed (Block 204). In the preferred implementation, the color ratio is the difference of two pixel color components to the sum of the same two pixel color components. In the most preferred implementation, the red and green pixel color components are used to score NAP in a cellular specimen stained with a solution of napthol AS-biphosphate salt and fast red violet LB and then counterstained with hematoxylin. Thus, the ratio may be expressed as $(R-G)/(R+G)$, although other color component combinations may be used. The color component selection preferably includes the two color components which best correspond to the marker identifying participate color (typically stain color) and the cell identifying color (typically counterstain color). The ratio identifies those pixels which are dominated by the first color component (red in the most preferred embodiment) from which the second color component (green in the most preferred embodiment) is subtracted. The ratio lies in the range of $-1$ to $+1$ where the ratio is positive for pixels dominated by the first color component, negative for pixels dominated by the second color component, and zero where the two components are equal.

Use of the color ratio permits the system and method of the present invention to process the pixels of the regularly shaped area to evaluate the amount of marker identifying precipitate without having to traverse the perimeter to identify all of the pixels in a candidate object of interest. Instead, the ratio of two color components, at least one of which corresponds to the color of the marker identifying precipitate, allows the system to identify the pixel values corresponding to the marker identifying precipitate without having to reference the geometry of the candidate object of interest. This permits the method of the present invention to evaluate each candidate object of interest more quickly and more accurately than methods that rely on geometry to identify pixels corresponding to the marker identifying precipitate.

Most preferably, a color ratio is only computed for those pixels having a two color component difference which is larger than a predetermined noise threshold. Preferably, the noise threshold is a small positive number and, most preferably the threshold is five (5). The effect of the noise threshold is to reduce the number of pixels in a white or dark area which may appear to have color indicative of the marker identifying precipitate. White or black pixels should have a value in which all of the color components are zero (0) or two hundred and fifty-five (255), respectively. As a result a two color component difference for a white or black pixel should be zero and the pixel not included in the color ratio normalization discussed below. However, electronic noise may cause a pixel that should be white to have a color component with a small, positive value or a pixel that should be black to have a color component that is slightly less than 255. If that color component with the noise induced value is the red component for the white pixel or the green component for the black pixel in the preferred two color component difference for NAP grading, then a small, positive ratio is computed for both the white and black pixel. These color ratios would then be included in the color ratio normalization and skew the results. This skewed ratio may then affect the grade for candidate object of interest and possibly the score for the cellular specimen. However, the noise threshold prevents the computation of the color ratio for the pixel as long as the two color component difference is less than the noise threshold. Additionally, the noise threshold reduces the likelihood that pixels from an overlapped cell are included in the grading and scoring of the cellular specimen. For example, pixels for a red blood cell that overlaps a candidate object of interest and which extends beyond the perimeter of the candidate object of interest are, typically, not intensely red. As a consequence, the noise threshold would eliminate those pixels of the red blood cell outside the candidate object of interest that are nominally red colored from the candidate object grading. This filtration is done without reference to the perimeter of the candidate object of interest.

Alternatively, pixels which are almost white or almost black may be considered white or black so they are not used for grading a candidate object of interest. This method determines whether the color component having the largest value is less than a white threshold or whether the color component having the smallest value is greater than a black threshold. For example, using a white threshold of 10, an almost white pixel having red, green and blue values of 9, 3, and 8, respectively, would be considered a white pixel with a two color component difference of zero (0) even though the actual red-green difference is six (6). Thus, a noise threshold of 5 would have included the color ratio for the pixel in the object grading but the white threshold of 10 would remove it from the grading. Likewise, a black threshold of two hundred and fifty (250) would classify pixels having a smallest color component of 250 or higher as black pixels and not compute a color ratio for the pixel.

The process of FIG. 4 then continues by summing all of the color ratios for the pixels having a positive, non-zero color ratio and dividing the sum by the number of pixels used to compute the sum (Block 208, 210, 212, 214). This normalized color ratio for the area is then compared to at least one threshold to determine the amount of marker identifying precipitate (Block 220). In the preferred embodiment for NAP for the stain and counterstain discussed above, there are four thresholds for the range of 0 to +1. These four thresholds divide the range into five sub-ranges which correspond to the five grades typically used to classify the intensity of the NAP precipitate. The grade for the area is then added to an object score (Block 224) and the process continues until a predetermined number of candidate objects of interest have been processed (Block 228). In the most preferred embodiment, the predetermined number of candidate objects of interest to evaluate the amount of NAP in a cellular specimen is one hundred (100) objects. The object score is then stored in association with the slide (Block 230) for later evaluation by a pathologist. Alternatively, the object score may be compared to a predetermined threshold which indicates whether the cellular specimen indicates the condition associated with the marker.

In the preferred embodiment of the present invention, the process of FIG. 4 is implemented in a C program which is downloaded to image processor 25 for execution, although other programming languages may be used. Additionally, the program may be executed on another processor of the system as long as the image data stored in image processor 25 is available for the program and/or hardware implementing the process of FIG. 4.

Figure 6:
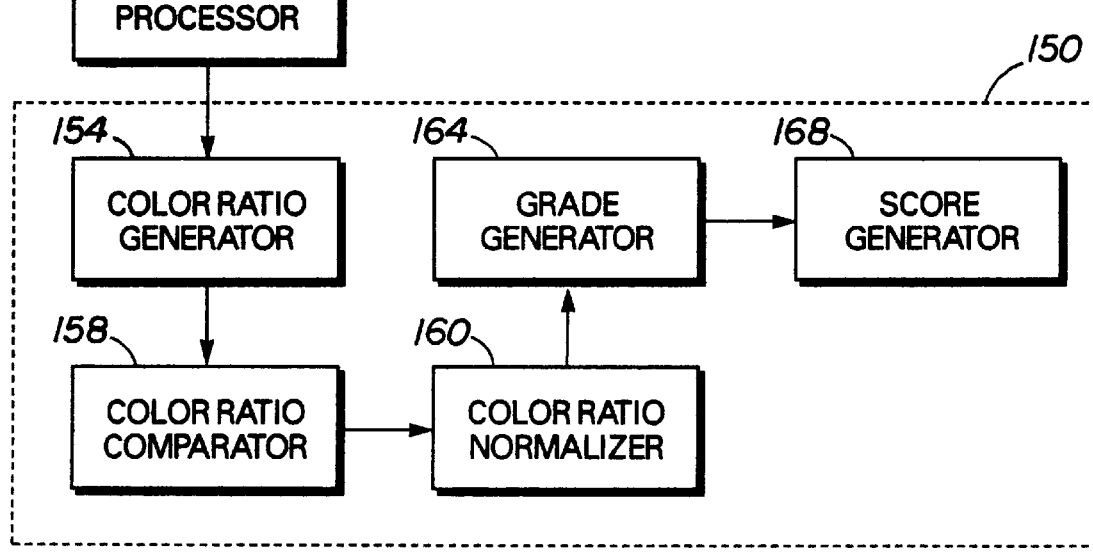
FIG. 6 is a block diagram of a cellular specimen grading system implementing the method of FIG. 4.

A system which may be used to implement the preferred method of the present invention is shown in FIG. 6. System 150 processes image data stored in image processor 25 to generate a score for a cellular specimen bound to a slide. Color ratio generator 154 computes the color ratios for pixels within a regularly defined area about a centroid for a candidate object of interest in the image data. Preferably, color ratio generator 154 includes a noise threshold to determine for which pixels a color ratio is computed. The computed color ratios are provided to color ratio comparator 158 which compares the color ratio to a positive, non-zero threshold to determine whether the color ratio is included in the normalized color ratio for the specimen. Those color ratios passed by comparator 158 are provided to color ratio normalizer 160 which sums the color ratios passed to it and divides by the number of color ratios passed to it. The normalized color ratio for a candidate object of interest is provided to grade generator 164 which compares the normalized color ratio to one or more thresholds and assigns a grade to the candidate object of interest. The assigned grade is provided to score generator 168. Score generator 168 sums the grades for a predetermined number of candidate objects of interest to generate an aggregate score which may be stored with data for the slide. The score may be used to determine whether the cellular specimen indicates a particular medical condition. The components of system 150 may be implemented in hardware or software or a combination thereof.

In use, laboratory technologists prepare a plurality of slides with cellular specimens which are treated to make a marker visually detectable. The slides are then loaded onto slide carriers and placed in the slide hopper of the automated microscope system. The system is initialized and slide carriers are fed to the motorized stage beneath the objective turret. The low magnification and high magnification processing is performed to identify and confirm candidate objects of interest. Images of a regularly shaped area centered about the centroid of a predetermined number of confirmed candidate objects are then graded using the method of the present invention. The aggregate score for the cellular specimen on the slide is then stored with an identifier for the slide and the next slide on the carrier is processed. Each slide on each carrier is processed until all slides in all of the carriers have been processed. At the end of the process, a montage of the confirmed candidate objects of interest for each slide, a grade for each object, a location for each object, and an aggregate score for each slide are stored in the computer subsystem. This information may be used by a pathologist to determine whether a cellular specimen indicates a specific medical condition or to review the objects on the slide which were graded.

While the present invention has been illustrated by the description of the preferred and alternative embodiments and while the embodiments have been described in considerable detail, it is not the intention of the applicant to restrict or anyway limit the scope of the appended claims to such detail. Additional advantages and modifications will readily appear to those skilled in the art. The invention's broader aspects are therefore not limited to the specific details, representative apparatus and method, or illustrative examples shown and described. Accordingly, departures may be made from such details without departing from the spirit or scope of applicant's general inventive concepts.

We claim:

1. A method for evaluating the amount of a visually detectable marker identifying precipitate in a cellular specimen bound to a microscope slide comprising the steps of:

obtaining a color digital image of a magnified view of a cellular specimen bound to microscope slide;

processing the color digital image to identify a plurality of candidate objects of interest in the cellular specimen;

identifying a centroid for identified candidate objects of interest in the plurality of candidate objects of interest;

computing a color ratio of at least two color components for each pixel of an area centered about each identified centroid;

computing an average color ratio for all pixels in the area centered about each centroid that have a computed color ratio that exceeds a predetermined color ratio threshold; and comparing the computed average color ratio to at least one intensity threshold to evaluate the amount of marker identifying precipitate in each area centered about each centroid.

2. The method of claim 1, the color ratio computing step further comprising the steps of:

computing a color ratio of a red pixel component to a green pixel component for each pixel.

3. The method of claim 1, the color ratio computing step further comprising the step of:

computing a color ratio of a difference between a first pixel color component and a second pixel color component to a sum of the first pixel color component and the second pixel color component for each pixel in the area.

4. The method of claim 3 wherein the first pixel color component is red and the second pixel color component is green.

5. The method of claim 3 wherein said comparing step compares the computed average color ratio is compared to a plurality of ordered thresholds to determine a grade for the amount of marker identifying precipitate in each area centered about each centroid.

6. The method of claim 5 further comprising the step of:

summing the grades for a plurality of areas to determine a score for the cellular specimen.

7. The method of claim 6 wherein the cellular specimen score is the sum of the grades for one hundred areas centered about one hundred centroids identified in the cellular specimen.

8. The method of claim 3 further comprising the step of:

comparing the two color component difference to a noise threshold; and computing the color ratio in response to the two color component difference being greater than the noise threshold.

9. The method of claim 3 further comprising the step of:

comparing a color component for a pixel having a largest value to a white threshold and a color component for the pixel having a smallest value to a black threshold to determine whether a color ratio for the pixel is computed.

10. A system for evaluating the amount of a visually detectable marker identifying precipitate in a cellular specimen bound to a microscope slide comprising:

an image processor for obtaining a color digital image of a magnified view of a cellular specimen bound to microscope slide;

means for identifying candidate objects of interest in the cellular specimen;

means for identifying a centroid for each candidate object of interest;

means for computing a color ratio of at least two color components for each pixel of an area centered about each identified centroid;

means for computing an average color ratio for all pixels in the area centered about each centroid that have a computed color ratio that exceeds a predetermined ratio threshold; and means for comparing the computed average ratio to at least one intensity threshold to evaluate the amount of marker identifying precipitate in each area centered about each centroid.

11. The system of claim 8 wherein said means for computing a color ratio is a means for computing a ratio of red pixel component to a green pixel component.

12. The system of claim 8 wherein said means for computing a color ratio is a means for computing a ratio of a difference between a first pixel color component and a second pixel color component to a sum of the first pixel color component and the second pixel color component.

13. The system of claim 10 wherein the first pixel color component is red and the second pixel color component is green.

14. The system of claim 10 wherein said means for comparing the computed average color ratio compares the computed average color ratio to a plurality of ordered thresholds to determine a grade for the amount of marker in each area centered about each centroid.

15. The system of claim 12 further comprising:

means for summing the grades for a plurality of areas to determine a score for the cellular specimen.

16. The system of claim 13 wherein said means for summing sums the grades for one hundred areas centered about one hundred centroids identified in the cellular specimen.

17. A method for evaluating the amount of a visually detectable marker identifying precipitate in a plurality of candidate objects of interest located in a digital image of a cellular specimen bound to a microscope slide comprising the steps of:

identifying a centroid for each candidate object of interest in a plurality of candidate objects of interest;

computing a color ratio of at least two color components for each pixel of an area centered about each identified centroid;

computing an average color ratio for all pixels in the area centered about each centroid that have a computed color ratio that exceeds a predetermined color ratio threshold; and comparing the computed average color ratio to at least one intensity threshold to evaluate the amount of marker identifying precipitate in each area centered about each centroid.

18. The method of claim 17 wherein the area centered about a centroid is a regularly shaped area.

19. The method of claim 17 wherein the regularly shaped area is a parallelogram.

20. The method of claim 17, the color ratio computing step further comprising the step of:

computing a color ratio of a difference between a first pixel color component and a second pixel color component to a sum of the first pixel color component and the second pixel color component for each pixel in the area.

21. The method of claim 19 wherein the first pixel color component is red and the second pixel color component is green.

22. The method of claim 19 wherein said comparing step compares the computed average color ratio is compared to a plurality of ordered thresholds to determine a grade for the amount of marker identifying precipitate in each area centered about each centroid.

23. The method of claim 21 further comprising the step of:

summing the grades for a plurality of areas to determine a score for the cellular specimen.

24. The method of claim 20 further comprising the step of:

comparing the two color component difference to a noise threshold; and computing the color ratio in response to the two color component difference being greater than the noise threshold.

25. The method of claim 20 further comprising the step of:

comparing a color component for a pixel having a largest value to a white threshold and a color component for the pixel having a smallest value to a black threshold to determine whether a color ratio for the pixel is computed.

26. A system for scoring the amount of a marker identifying precipitate in a cellular specimen bound to a microscope slide comprising:

a color ratio generator for computing color ratios for pixels within an area centered about a centroid for a candidate object of interest in image data of a magnified view of the cellular specimen;

a color ratio comparator for comparing the computed color ratios to a predetermined threshold to determine which color ratios are included in a normalized color ratio;

a color ratio normalizer for generating a normalized color ratio;

a grade generator for generating a grade for the candidate object of interest from the normalized color ratio; and a score generator for generating a score indicative of an amount of a marker identifying precipitate in the cellular specimen by summing grades for a predetermined number of candidate objects of interest.

27. The system of claim 26 said color ratio generator further comprising:

a noise threshold used by the color ratio generator to determine whether a color ratio is computed for a pixel.

28. The system of claim 26 said color ratio generator further comprising:

a white threshold and a black threshold which are used by the color ratio generator to determine whether a color ratio is computed for a pixel.

29. A method for evaluating the amount of a visually detectable marker identifying precipitate in a cellular specimen bound to a microscope slide comprising the steps of:

obtaining a color digital image of a manified view of a cellular specimen bound to microscope slide;

processing the color digital image to identify a plurality of candidate objects of interest in the cellular specimen;

identifying a centroid for identified candidate objects of interest in the plurality of candidate objects of interest;

computing a color ratio for a pixel in an area centered about each identified centroid in response to a largest color component value for the pixel being greater than a white threshold and a smallest color component value for the pixel being less than a black threshold, the color ratio being a ratio of a difference between a first pixel color component and a second pixel color component to a sum of the first pixel color component and the second pixel color component;

computing an average color ratio for all pixels in the area centered about each centroid that have a computed color ratio that exceeds a predetermined color ratio threshold; and comparing the computed average color ratio to at least one intensity threshold to evaluate the amount of marker identifying precipitate in each area centered about each centroid.

30. A system for scoring the amount of a marker identifying precipitate in a cellular specimen bound to a microscope slide comprising:

a color ratio generator for computing color ratios for pixels within an area centered about a centroid for a candidate object of interest in image data of a magnified view of the cellular specimen, the color ratio generator having a white threshold and a black threshold that are used by the color ratio generator to determine whether a color ratio is computed for a pixel;

a color ratio comparator for comparing the computed color ratios to a predetermined threshold to determine which color ratios are included in a normalized color ratio;

a color ratio normalizer for generating a normalized color ratio;

a grade generator for generating a grade for the candidate object of interest from the normalized color ratio; and a score generator for generating a score indicative of an amount of a marker identifying precipitate in the cellular specimen by summing grades for a predetermined number of candidate objects of interest.

* * * * *

UNITED STATES PATENT AND TRADEMARK OFFICE
CERTIFICATE OF CORRECTION

PATENT NO.    : 6,151,405                                                    Page 1 of 1
DATED         : November 21, 2000
INVENTOR(S)   : James Douglass et al.

It is certified that error appears in the above-identified patent and that said Letters Patent is hereby corrected as shown below:

Title page,
Please replace "Related U.S. Application Data,
[63] Continuation-in-part of application No. 08/758,436, Nov. 29, 1996." with
-- Related U.S. Application Data,
[63] Continuation-in-part of application No. 08/758,436, Nov. 27, 1996. --.

Column 1,
Line 5, please delete "Nov. 29, 1996", and replace it with -- Nov. 27, 1996 --.

Signed and Sealed this

Thirtieth Day of March, 2004

JON W. DUDAS
*Acting Director of the United States Patent and Trademark Office*